United States Patent
Crouch et al.

(10) Patent No.: US 7,557,570 B2
(45) Date of Patent: Jul. 7, 2009

(54) SYSTEM AND METHOD FOR PRODUCING COLOR CONTOUR MAPS OF SURFACE DEFECTS OF HIGH PRESSURE PIPELINES

(75) Inventors: Alfred E. Crouch, San Antonio, TX (US); Todd Goyen, San Antonio, TX (US); Patrick C. Porter, Houston, TX (US); Shawn Laughlin, The Woodlands, TX (US)

(73) Assignee: The Clock Spring Company L.P., Houston, TX (US)

( * ) Notice: Subject to any disclaimer, the term of this patent is extended or adjusted under 35 U.S.C. 154(b) by 268 days.

(21) Appl. No.: 11/556,307

(22) Filed: Nov. 3, 2006

(65) Prior Publication Data

US 2007/0126422 A1 Jun. 7, 2007

Related U.S. Application Data

(60) Provisional application No. 60/732,959, filed on Nov. 3, 2005.

(51) Int. Cl.
*G01N 27/82* (2006.01)
*G01B 7/06* (2006.01)

(52) U.S. Cl. .................. 324/229; 324/221; 324/240; 324/202

(58) Field of Classification Search ........... 324/220, 324/228–243, 202, 221
See application file for complete search history.

(56) References Cited

U.S. PATENT DOCUMENTS

| | | | |
|---|---|---|---|
| 3,939,404 A | 2/1976 | Tait | |
| 4,064,452 A | 12/1977 | Toth | |
| 4,134,067 A | 1/1979 | Woodbury | |
| 4,247,819 A | 1/1981 | Shimada et al. | |
| 4,258,319 A | 3/1981 | Shimada et al. | |
| 4,312,231 A | 1/1982 | Kawashima et al. | |
| 4,368,429 A | 1/1983 | Jamison | |
| 4,423,636 A | 1/1984 | Plante | |
| 4,425,545 A | 1/1984 | Scalese | |
| 4,467,281 A * | 8/1984 | Davis et al. ............ | 324/232 |
| 4,495,587 A | 1/1985 | Plante et al. | |
| 4,523,473 A | 6/1985 | Chamuel | |
| 4,578,643 A | 3/1986 | Junker et al. | |
| 4,608,534 A | 8/1986 | Cecco et al. | |
| 4,628,260 A | 12/1986 | Kimato et al. | |
| 4,631,688 A | 12/1986 | Boehm et al. | |
| 4,646,013 A | 2/1987 | Tornbloom | |
| 4,687,992 A | 8/1987 | von Bernus et al. | |
| 4,706,021 A | 11/1987 | Chamuel | |

(Continued)

FOREIGN PATENT DOCUMENTS

JP 11051905 A * 2/1999

*Primary Examiner*—Jay M Patidar
(74) *Attorney, Agent, or Firm*—Tim Headley; Headley IP Law

(57) ABSTRACT

A system for mapping a surface defect in an electrically-conducting material by measuring a change in the resonance of the material includes a flexible printed circuit board and a two dimensional array of transducers printed on the flexible circuit board, wherein each element of the array includes two transducer coils in a paired arrangement. A receive circuit connected to the coils is tuned to a resonant frequency, and the transducer coils operate in a send/receive mode. In another feature of the invention, there are means for converting a change in measured resonance to a visual display of the depth and width of the surface defect.

8 Claims, 3 Drawing Sheets

U.S. PATENT DOCUMENTS

| | | | |
|---|---|---|---|
| 4,837,510 A | 6/1989 | Tornblom | |
| 4,851,774 A | 7/1989 | Tornblom | |
| 4,853,634 A | 8/1989 | Tornblom | |
| 4,864,235 A | 9/1989 | Tornblom | |
| 4,954,778 A | 9/1990 | Champonnois et al. | |
| 4,965,519 A | 10/1990 | Tornblom | |
| 5,047,719 A * | 9/1991 | Johnson et al. | 324/242 |
| 5,182,513 A | 1/1993 | Young et al. | |
| 5,184,070 A | 2/1993 | Besendorfer et al. | |
| 5,262,722 A | 11/1993 | Hedengren et al. | |
| 5,345,514 A | 9/1994 | Mahdavieh et al. | |
| 5,363,040 A | 11/1994 | Horn | |
| 5,389,876 A * | 2/1995 | Hedengren et al. | 324/242 |
| 5,446,378 A | 8/1995 | Reich et al. | |
| 5,452,182 A * | 9/1995 | Eichelberger et al. | 361/749 |
| 5,537,334 A | 7/1996 | Attaoui et al. | |
| 5,670,879 A | 9/1997 | Zombo et al. | |
| 5,793,206 A | 8/1998 | Goldfine et al. | |
| 6,067,857 A | 5/2000 | Cooper et al. | |
| 6,344,739 B1 * | 2/2002 | Hardy et al. | 324/220 |
| 6,429,646 B1 | 8/2002 | Han | |
| 6,519,535 B1 | 2/2003 | Petri et al. | |
| 6,541,963 B2 * | 4/2003 | Mednikov et al. | 324/225 |
| 6,545,467 B1 | 4/2003 | Batzinger et al. | |
| 6,812,697 B2 | 11/2004 | McKnight et al. | |
| 6,914,427 B2 * | 7/2005 | Gifford et al. | 324/242 |
| 7,010,987 B2 | 3/2006 | Antonelli et al. | |
| 2002/0027436 A1 | 3/2002 | Taylor | |
| 2003/0071615 A1* | 4/2003 | Schlicker et al. | 324/242 |
| 2003/0164700 A1 | 9/2003 | Goldfine et al. | |
| 2003/0227288 A1 | 12/2003 | Lopez | |
| 2004/0056656 A1 | 3/2004 | McKnight et al. | |
| 2004/0066188 A1 | 4/2004 | Goldfine et al. | |
| 2004/0066189 A1 | 4/2004 | Lopez | |
| 2004/0075432 A1 | 4/2004 | Loud | |
| 2004/0139805 A1 | 7/2004 | Antonelli et al. | |
| 2004/0232911 A1 | 11/2004 | Schlicker et al. | |
| 2004/0257072 A1 | 12/2004 | Samson | |
| 2005/0146324 A1 | 7/2005 | Goldfine et al. | |
| 2005/0206374 A1 | 9/2005 | Roney, Jr. et al. | |
| 2005/0231194 A1 | 10/2005 | Baldi et al. | |
| 2006/0103389 A1 | 5/2006 | Bespalov et al. | |
| 2006/0170420 A1 | 8/2006 | Nishimizu et al. | |

\* cited by examiner

SYSTEM AND METHOD FOR PRODUCING COLOR CONTOUR MAPS OF SURFACE DEFECTS OF HIGH PRESSURE PIPELINES

CROSS-REFERENCES TO RELATED APPLICATIONS

This patent application claims the benefit of provisional patent application Ser. No. 60/732,959, filed Nov. 3, 2005.

STATEMENT REGARDING FEDERALLY SPONSORED RESEARCH OR DEVELOPMENT

None.

REFERENCE TO A "SEQUENCE LISTING," A TABLE, OR A COMPUTER PROGRAM LISTING APPENDIX SUBMITTED ON A COMPACT DISC AND AN INCORPORATION BY REFERENCE OF THE MATERIAL ON THE COMPACT DISC

None.

BACKGROUND OF THE INVENTION (1) Field of the Invention

The invention relates to devices for measuring the geometry of defects that have altered the surface of an electrically conducting pipe.

(2) Description of the Related Art

Pipelines and other structures used in the petrochemical industry are generally made of steel, and are pressurized. Defects such as corrosion, gouges, cracks, or other imperfections or features that remove or alter a portion of the steel can affect the ability of the pipe or structure to operate safely. When a defect or imperfection is discovered it must be assessed using engineering techniques defined in the operating code covering the installation, or by using methods developed and approved by the operator. This assessment requires a calculation using the material properties and design standards of the original construction, and measurements of the defect or imperfection.

Defect assessment in high pressure pipes is typically performed for corrosion, gouges or metal loss defects, and typically follows one of three industry-accepted methods. The most common is B31G (ASME B31G, Manual for Determining the Remaining Strength of Corroded Pipelines). This assessment technique requires the length and maximum depth of a metal loss or corrosion defect, which, with pipe material information and original design standards, can be used to calculate a safe operating pressure for the defect.

More complex assessment methods can be used to minimize unnecessary repairs. Using modified material properties and a different shape factor, a modified assessment can be made that is less conservative than the original B31G. This is known as the 0.85 dt method. This technique also requires that the length of the defect or imperfection and the maximum depth of the defect or imperfection be known. These measurements are used to calculate a safe operating pressure for the defect or imperfection.

The assessment technique with the least variability is the exact or effective area technique. This technique uses the exact cross-sectional area of the defect. The area is determined from an axial depth profile which uses the maximum corrosion depth at each axial measurement spacing. This axial depth profile is projected to a linear representation of the defect, and then the area of metal loss is calculated.

Each of these methods is defined in detail in the appropriate code. Each method specifies the defect measurements required to make the calculation to determine the effect of the defect or imperfection on the safety of the pipeline or installation.

Regardless of which assessment method is used, the input data are usually provided by local measurements on the outside of the pipe or structure.

The simplest case is that of a single isolated corrosion pit or area of metal loss. A scale measures the length of the defect area. A dial extension gage (pit gage) is placed over the pit (assuming the base will span the pit) and the maximum depth read and recorded. Slightly more complicated is the case of several overlapping pits or metal loss areas or a small patch of corrosion. In such cases, the length can still be measured with a scale. An attachment, such as a bridging bar, often spans the entire defect or imperfection, providing a reference surface from which to measure depth. It is not always possible to readily locate the deepest pit or metal loss within the grouping from a visual examination, so several independent depth measurements must be taken. It is also difficult to determine if defects in close proximity interact as defined by the rules outlined in the appropriate codes.

When corrosion or metal loss is extensive and an exact area assessment is needed, it is essential that the defect be accurately mapped to form a contour plot. In these cases, a rectangular grid is drawn or painted on the pipe or structure surface, including the corroded or metal loss area. Depth measurements are taken at each grid intersection. From this array of measurements, either manual or computer-aided processing is used to construct a contour map. The contour map is then used to assess the defect, and calculate a safe operating pressure. All these manual measurement methods are laborious, time-consuming, and error prone.

There have been some devices that automate some aspects of inspections, using eddy current arrays, as, for example, in the following patents, which are incorporated herein by this reference: U.S. Pat. Nos. 5,793,206, 5,182,513, and 5,262,722. However, these all have various limitations, as set forth in U.S. Patent Application No. 20040232911.

U.S. Pat. No. 6,545,467, which is incorporated herein by this reference, states in the abstract, "A flexible eddy current array probe is attached to the contoured exterior surface of the backing piece such that the probe faces the contoured surface of the workpiece to be inspected when the backing piece is disposed adjacent to the workpiece. The backing piece is then expanded volumetrically by inserting at least one shim into a slot in the backing piece to provide sufficient contact pressure between the probe and the workpiece contoured surface to enable the inspection of the workpiece contoured surface to be performed." However, the method disclosed in this patent is primarily concerned with ensuring coupling between a flexible eddy current array probe and a workpiece to be inspected. This patent does not disclose a two-dimensional eddy current array, does not disclose how to use such an array, does not provide the means to map defects, and does not use the flexible substrate to reestablish the contour of the workpiece.

Another device that uses eddy current arrays has been disclosed in the following patent applications, which are incorporated herein by this reference: U.S. Patent Application Nos. 20030164700 and 20040232911. These patent applications disclose a device that has essentially identical sensor arrays with sensing elements aligned in proximity to the drive elements, and conductive pathways that promote cancellation of undesired magnetic flux. These references do not disclose how to reestablish the original surface contour of a pipe, nor do they disclose any way to expand the dynamic range of the testing device.

Another device that uses eddy current arrays has been disclosed in the following patent application, which is incorporated herein by this reference: U.S. Patent Application No. 20060170420, which states in the abstract, "An eddy current testing probe has a flexible substrate adapted to face to a surface of a test article, a plurality of coils which are fixed to the flexible substrate and energized one of which is capable of being changed sequentially, a pressing member for pressing the substrate toward the test article, an elastic member arranged between the substrate and the pressing member, and a movement limiting member for limiting a movement of the pressing member toward the test article." The device disclosed in this patent is again concerned about pressing an eddy current probe against a workpiece, or "test article", and the attendant problems with exerting such pressure. The patent does not disclose how to map the dimensions of surface defects.

In light of the foregoing, a need remains for a flexible two-dimensional eddy current array that 1) provides a means to map defects on a pipe, 2) uses the flexible substrate to reestablish the original surface contour of a pipe, and 3) provides means to expand the dynamic range of the eddy current array.

BRIEF SUMMARY OF THE INVENTION

A system for mapping a surface defect in an electrically-conducting material by measuring a change in the resonance of the material comprises: a flexible printed circuit board; and a two dimensional array of transducers printed on the flexible circuit board, wherein each element of the array comprises two transducer coils in a paired arrangement. A receive circuit connected to the coils is tuned to a resonant frequency, and the transducer coils operate in a send/receive mode. In another feature of the invention, there are means for converting a change in measured resonance to a visual display of the depth and width of the surface defect.

DETAILED DESCRIPTION OF THE INVENTION

Figure 1:
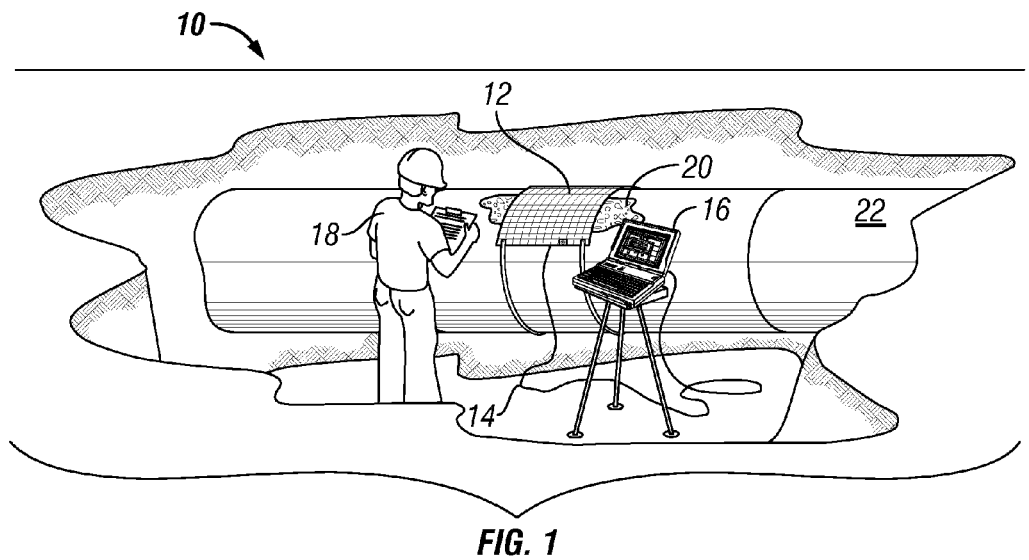
FIG. 1 is an overview showing the conformable eddy current array of the present invention being used to measure a defective surface area of a pipe.

In FIG. 1, the system 10 of the present invention includes a flexible eddy-current sensor array 12, and a USB cable 14 that connects the array 12 to a laptop computer 16. The array 12 receives power from the laptop computer 16 through a USB port. As shown, the system 10 is used by an operator 18 to detect the extent of surface corrosion or defect 20 on an underground pipe 22.

Figure 2:
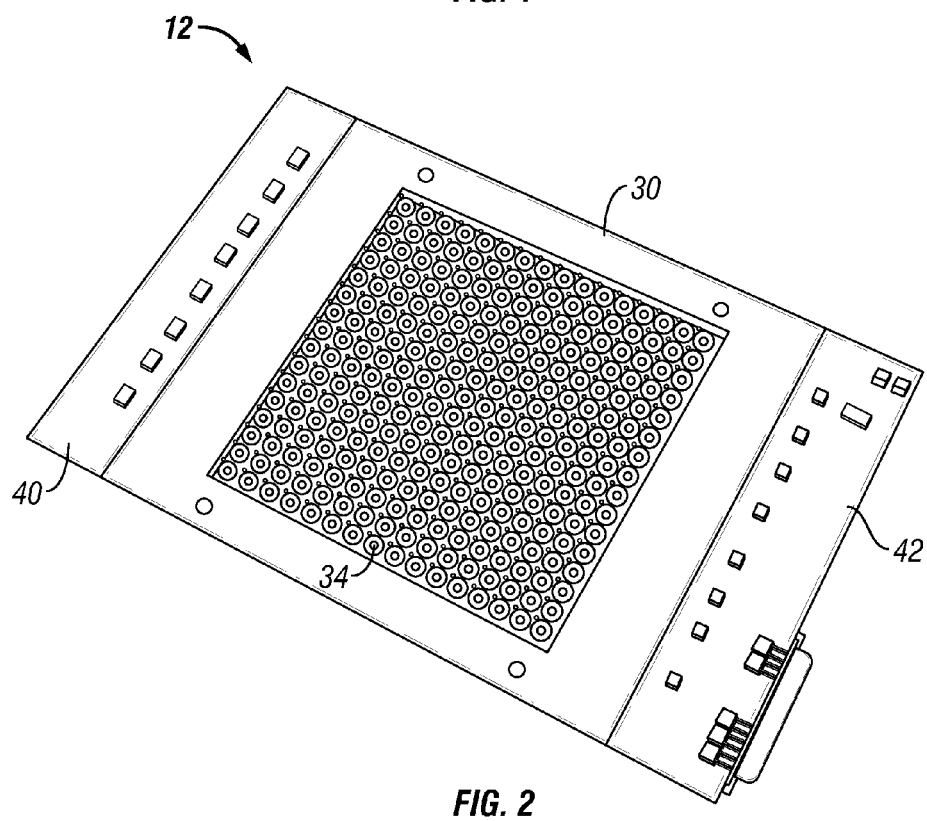
FIG. 2 is a schematic diagram of the conformable array of the present invention.

Referring now to FIG. 2, the array 12 includes a flexible section 30. Although the flexible section 30 can be of any size and number of transducers, in the preferred embodiment the flexible section 30 contains 512 coils 32 arranged in 256 coil pairs 34, with connections allowing each coil to sense pit depth over the area beneath it. The coil pairs 34 are arranged in a square grid with 16 rows and 16 columns. The grid measures 6-inches on each side. The number and size of the coil pairs can be altered to make larger or smaller versions of the flexible section 30 or to alter the resolution of the entire system 10. Each coil pair 34 consists of a send coil 32$a$ and a receive coil 32$b$, one on top of the other, exactly aligned.

The flexible section 30 is a printed circuit that contains the coil pairs 34. The flexible section 30 will conform to the shape of the pipe or structure being assessed, and is stiff enough to reestablish the original contour of the pipe or structure. The flexible section 30 is a printed circuit board, manufactured by the Speedy Circuits Division of PJC Technologies, Inc., 5331 McFadden Avenue, Huntington Beach, Calif. 92649. The section 30 provides the reference surface from which lift-off measurements can be referenced, representing the depth of the defect 20 or feature immediately under a coil pair 34. The axial and circumferential position of each measurement is acquired from the position of the coil pair 34 within the section 30.

Figure 3A:
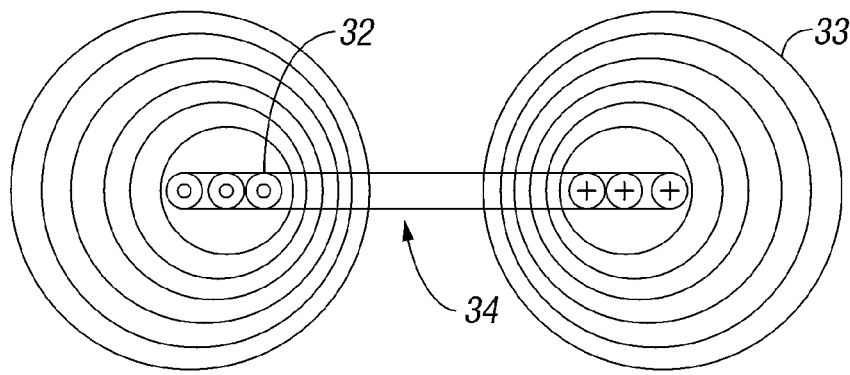
FIG. 3 is a schematic diagram of the individual coils that comprise the array shown in FIG. 2.
Figure 3B:
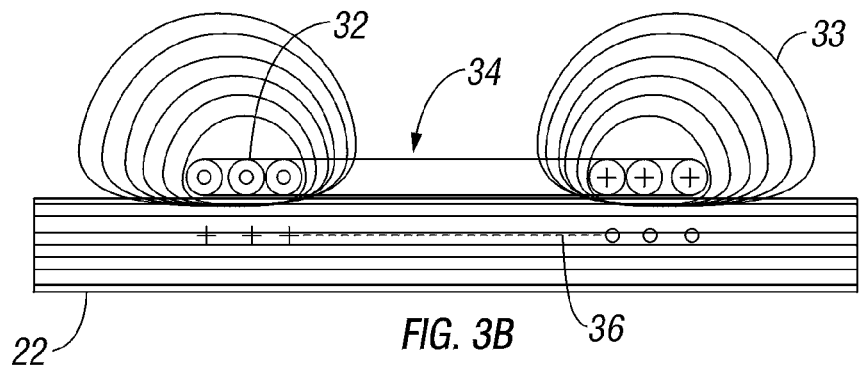

Referring now to FIG. 3, eddy current lift-off is the method of pit depth or metal loss measurement in the pipe 22 used by the conformable array 12. If an alternating electrical current flows in a coil 32, a magnetic field 33 is created about the coil 32 (FIG. 3A). If the coil 32 is placed near an electrically conducting material, such as the pipe 22, the magnetic field 33 penetrates the pipe 22 and causes reaction currents 36 (eddy currents) to flow in the pipe 22 (FIG. 3B). The effect of this eddy current 36 is to oppose the force or current that created it, which is manifest as a change in the impedance of the driving coil 32$a$. The amount of change depends, among other things, on the distance between the coil and the electrically conducting material 22. For crack-like defects the crack itself will impede the eddy current, resulting in a change of coupling, and a sensor change that can be measured.

Figure 4A:
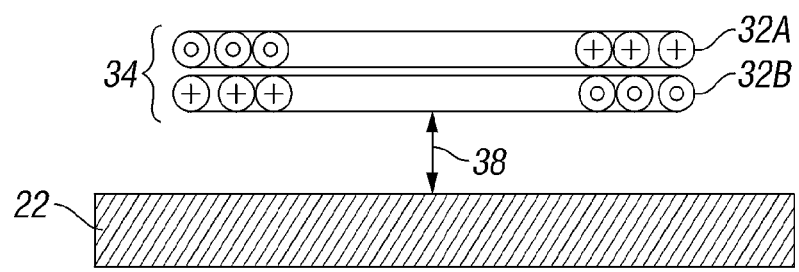
FIG. 4 is a schematic diagram showing the individual coils and the depth of the surface defect of a pipe.
Figure 4B:
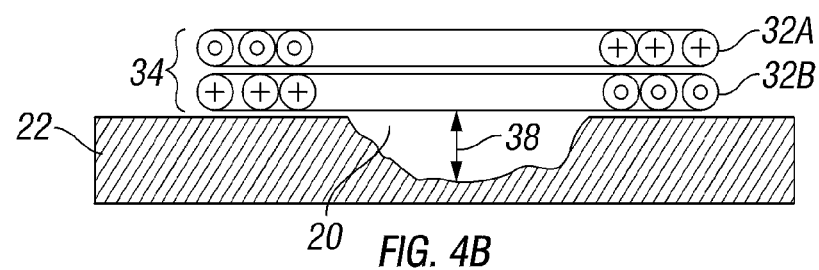

Referring now to FIG. 4A, if a single coil 32 of a coil pair 34 is subject to an alternating current, and is placed over an electrically conducting material 22, the coupling between the active coil 32$a$ and the second coil 32$b$ of the pair 34 will be altered leading to changes that are manifest as a change in the impedance of the coil 32. This change in impedance may be detected as a measure of the distance 38 from the coil pair 34 to the conducting surface 22. Referring now to FIG. 4B, if the coil pair 34 is placed near the surface of the conducting material 22 with a defect 20 present, the coupling change will be a function of the depth 38 and size of the defect 20.

Referring again to FIG. 2, in addition to the flexible section 30, the array 12 includes two rigid sections 40, 42 that contain the electronics to address each of the coils 32 individually. This requires thirty-four 16-channel multiplexers. Sixteen 16-channel multiplexers are needed to address the 256 send coils 32$a$ with one additional 16 channel multiplexer being required to ensure that only one of the multiplexers is active at any given time. The same holds true for the receive coils 32$b$. Other systems on the rigid sections 40, 42 generate a sine wave signal, filter the analog portion of the circuits to minimize interference, provide a USB interface, regulate and filter power supplies for both the digital circuits and the analog circuits, and provide oscillators to provide clock and timing for the digital systems.

Figure 5:
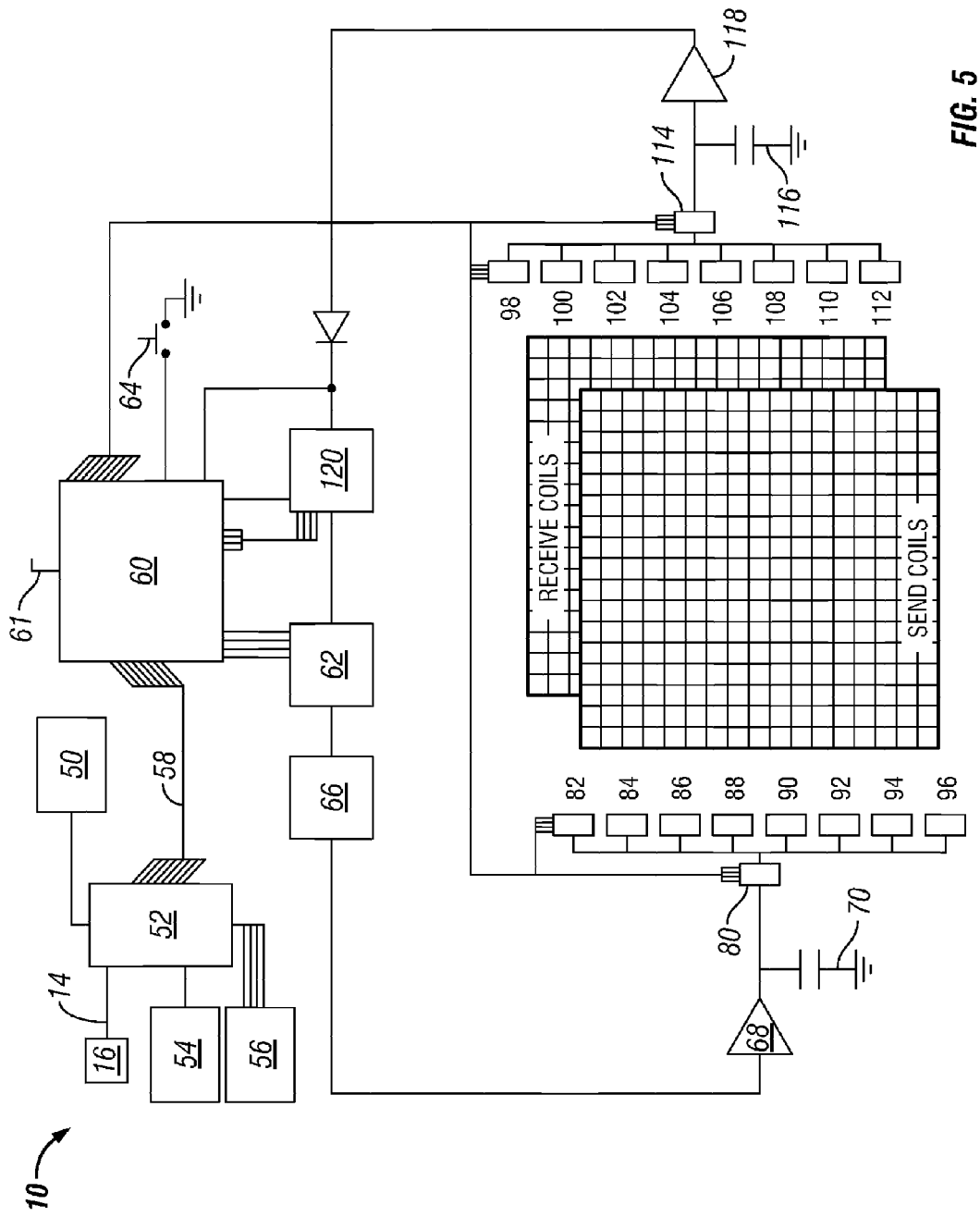
FIG. 5 is a schematic diagram of the electronics that control the eddy current array.

Referring now to FIG. 5, these systems of the rigid sections 40, 42 are shown. The laptop computer 16 connects via the wire 14 to the rigid sections 40, 42. Power distribution chip 50 protects the sections 40, 42 and the laptop computer 16 from power spikes that can be caused by capacitive loads.

USB interface chip 52 is model no. FT245BM, manufactured by FTDI. Chip 52 sends and receives data from and to the laptop 16. Oscillator 54 is a 6 MHz oscillator to operate the chip 52. EEPROM 56 is a 1K serial EEPROM that can be programmed from the USB chip 52. The EEPROM 56 tells the USB chip 52 that it is dealing with a Conformable Array. Data lines 58 are outputs from a microcontroller 60. This is where the coil data is sent from the microcontroller 60 for transfer to the laptop computer 16. Connector 61 is used to program the microcontroller 60.

The microcontroller 60 is model no. MSP430X14X, manufactured by Texas Instruments. The microcontroller 60 controls all the functions of the array 12. The microcontroller 60 is used to address multiplexers that select a single coil pair 34 for activation. The microcontroller 60 sends a digital stream to a direct digital synthesizer 62, telling it to output a 4.2 MHz sine wave. The synthesizer 62 is model no. AD9834, manufactured by Analog Devices. The microcontroller 60 sends an output voltage via a 4-channel multiplexer, model no. ADG704, manufactured by Analog Devices. The multiplexer simply outputs 2.5 volts, which is connected to a lamp in a switch 64 through various resistors that simply increase the current to the lamp causing it to flicker or flash. The switch 64 is a data acquire button. When it is depressed it takes 3.3 volts on one of the resistors to ground, which then takes a pin of the microcontroller 60 to ground, initiating data capture.

The sine wave from the digital synthesizer 62 is output into a 6 pole Butterworth low pass filter 66. The filter 66 is made from model no. AD8039, manufactured by Analog Devices. The filter 66 removes signals at a frequency greater than 7 MHz. The output of the filter 66 is directed to a high pass filter that removes signals below 106 kHz, and is then input to a high-speed, high-current buffer amplifier 68 to provide the necessary drive current to the send coil 32a. The amplifier 68 is model no. BUF634, manufactured by Texas Instruments. A capacitor 70, 1000 pF, creates a resonant circuit with the drive coil at 4.2 MHz.

The output of the drive amplifier 68 is routed to the input of a 16-channel multiplexer 80, model no. ADG706, manufactured by Analog Devices.

The multiplexer 80 connects to sixteen 16-channel multiplexers, 82-112, which are each model no. ADG726, manufactured by Analog Devices. These multiplexers 82 to 112 are in a dual 16-channel packages.

Each of the multiplexers 82-112 is connected to a row of coils 32. The lowest 4 bits of the binary address counter cause each of the 16 multiplexers 82-112 to address one coil 32 of each row at a time. All sixteen multiplexers 82-112 are doing this coil sweep continuously and at the same time. The multiplexer 80 ensures that only one coil 32 is being activated at any given time. The multiplexer 80 couples the output of the driver amp 68 to a single multiplexer 82-112 at a time. For example, on initial startup the binary address count is 0000 0000. The lowest 4 bits, 0000 to 1111 address the A1 to A16 outputs of the multiplexers 82-112 and the top 4 bits, 0000 address the multiplexer 80 to output drive signal to only the first of the multiplexers 82-112. As the count progresses the driver signal remains connected to the same multiplexer until the bottom 4 bits have reached 1111, which will be the sixteenth coil in row 1. At this time the bottom 4 bits return to 0000 but the top 4 bits change to 1000. This then routes the drive signal to the second multiplexer of the group 82-112, and the process begins again. In this manner all coils are independently activated.

The output of the drive amplifier 68 is also routed to the input of a 16-channel multiplexer 114, model no. ADG706, manufactured by Analog Devices.

The output of the multiplexer 114 is the input to a 1000 pF capacitor 116, which is used to create a resonant circuit with the inductance of the receive coil at 4.2 MHz. The output of the multiplexer 114 is also the input to a non-inverting amplifier 118, model no. AD8038, manufactured by Analog Devices. A half-wave rectifier at the output of the amplifier 118 converts the AC 4.2 MHz output signal to a DC level, which is the input to a dual operational amplifier 120, model no. AD8572, manufactured by Analog Devices. The first stage is simply a non-inverting amplifier with a digitally controlled gain. The gain is set by a digital potentiometer, which takes its gain setting from the microcontroller. The output of stage 1 is also the input to the microcontroller. The output of stage 1 is the input to the second stage of this amplifier. This second stage is a low pass filter with a cutoff frequency of 1.2 kHz. This filter ensures a cleaner signal than may be available at the stage 1 output. This output is input to the microcontroller. In video mode the output of stage 1 input of the microcontroller is the active port. When the acquire data button 64 is depressed it makes the output of stage 2 of the final stage of the receive amplifier the active port. At this time the microcontroller 60 samples each received signal multiple times and averages the response. This average value is then sent to the USB interface chip 52 to be sent to the laptop computer 16.

In operation, the laptop computer 16 is used to acquire the data from each coil pair 34. When these measurements are acquired, they are input to the conformable array analysis software where the signal is compensated according to the response curve previously established by a calibration procedure to produce an accurate map of the defect 20 or imperfection being assessed. This defect map can then be used to assess the defect 20 or imperfection and determine the affect that the defect or imperfection will have on the integrity of the structure being assessed. The software produces a contour map of the defect 20. The map identifies the location and depth of all features within the scan area, and calculates the maximum safe operating pressure if the structure is a high pressure pipeline 22. The software allows an operator to calibrate measurements and record other pertinent information for record keeping purposes.

Prior to device operation each of the 256 transducer coil pairs 34 must be calibrated to develop the individual response curve for that transducer pair 34. This is done by providing a series of known distances from mild steel (or material similar to the material of the structure being assessed if the structure is made from electrically conducting material other than steel) to the coil pairs (called "lift-off") and measuring the receiver response. As calibration points are acquired for various lift-off distances they are fit to a polynomial curve. When sufficient calibration points are acquired, the coefficients of the polynomial curve are calculate and stored. Each transducer pair 34 will have a set of four polynomial coefficients which define its response to distance between the coil pair and the conducting surface. When calibration is complete, the calibration coefficients are written to, and stored in, the microprocessor on the array printed circuit card. This calibration data will reside with the array 12 during its life or until such time as a new calibration procedure is executed Although this description applies to an array consisting of 256 transducers arranged in 16 rows and 16 columns, designed for a resonant frequency of 4.2 MHz, the size of the array can be changed, and the resonant frequency can be changed.

When the array 12 is first activated by the laptop computer 16, the display and analysis software requests calibration information from the microprocessor 60. The microprocessor 60 sends the stored calibration coefficient data back to the array software through the USB cable 14 where it will be stored and used to process that scan. (The calibration data is stored in the microprocessor 60 using a calibration procedure applied to each assembly prior to use.)

The laptop computer 16 sends a "New Scan" command to the Conformable Array circuit board through a USB cable. The laptop computer 16 provides power to the electronics on the array printed circuit board through the USB cable 14. The "New Scan" command initiates the microprocessor 60 on the array 12 which in turn enables thirty-four 16-channel multiplexers. Sixteen 16-channel multiplexers are needed to address the 256 send coils with one additional 16 channel multiplexer being required to ensure that only one of the multiplexers is active at any given time. This ensures that only one coil is active. The array cycles through all 256 coils sequentially. The same holds true for the receive coils.

The send coils 32a and receive coils 32b are printed on the printed circuit card, one on top of the other, exactly aligned. The microprocessor enables a Direct Digital Synthesis (DDS) system located on the array. The DDS is programmed to output a sine wave drive signal at a frequency of 4.2 MHz and of known fixed amplitude. The frequency (4.2 MHz) is chosen such that the "send coil" 32a resonates with a 1000 pF capacitor in air. The receiver coil 32b also resonates with a 1000 pF capacitor in air. This 4.2 MHz signal is amplified and buffered and used to drive each of the 256 sender transducers sequentially in turn. The individual transducers are addressed by the microprocessor 60. The send and receive transducers of a sensor pair 34 are activated in unison. When the array is in close proximity to electrically conducting material the electromagnetic coupling between the coils 32 will be altered and the impedance of the transducer coils changed. The coils will no longer be resonant with the 1000 pF capacitors, and the amplitude of the coupled signal from the receive coil will change. Operating in the resonance range increases the dynamic range of the system 10. The magnitude of the change will be proportional to the change in inductance of the coil which is proportional to the distance 38 between the coil 32 and the conducting material 22. The receiver signal is rectified and filtered to provide a DC voltage proportional to lift-off. In the video scan mode the microprocessor will digitize the DC level and send it to the Conformable Array software for viewing. The software will read the amplitude of the signal and apply the appropriate compensation coefficients previously received from the microprocessor prior to displaying the signal as a color contour map. After compensation, the displayed signal will be proportional to the depth 38 of the defect 20. In this viewing mode each transducer 34 is scanned once by the microprocessor. When the acquire data command is sent to the microprocessor an additional filter is activated to remove minor ripple from the DC level and each receive transducer 34 is scanned multiple times, and an average value stored in the microprocessor. When all 256 transducers 34 are scanned the full data set is sent to the display software for visual inspection and analysis.

In operation the pipe 22 or other structure to be investigated is exposed or otherwise made available to the technician using the conformable eddy current array 12. The pipe 22 or structure is cleaned to remove lose debris and electrically conducting deposits that may exist in the defect 20 or imperfection being assessed. The conformable eddy current array 12 is attached to a laptop computer 16, and operated from the conformable array software residing on the laptop computer.

The conformable array 12 is positioned over the defect 20 to be assessed. A contour map representing the length, width, and depth of the defect 20 is visible to the operator on the laptop computer. The operator presses the acquire data button 64 on the array 12. The conformable array 12 takes and averages multiple readings from each transducer 34, and sends the final data to the software. If the structure being evaluated is a pipe 22, the software will immediately calculate the affect of the defect 20 on the operating properties of the pipe using commonly applied methods. The system 10 will alert the operator to input certain calibration measurements to ensure accuracy of the readings. If the area to be assessed is larger than the size of the active portion of the array 12, it can be assessed using multiple scans with the array 12 being carefully repositioned between each scan. The software is capable of stitching the multiple scans into a singe contour map of the defect 20.

The invention claimed is:

1. A method of producing a color contour map showing the locations, length, width, and depth of all surface defects within a chosen area of the surface of a high pressure pipeline, comprising the steps of:
   a. Calibrating each coil pair, each coil pair consisting of a send transducer coil aligned on top of a receive transducer coil, in a flexible array of transducer coil pairs to produce calibration coefficients for each pair;
   b. Storing the calibration coefficients in a microprocessor connected to the flexible array;
   c. Placing the flexible array of transducer coil pairs on the chosen area of the surface of the pipeline;
   d. Tuning a receive circuit connected to the coils to a resonant frequency;
   e. Sequentially and independently activating each coil, and activating in unison the send transducer coil and the receive transducer coil of each coil pair, operating the transducer coil pairs in a send/receive mode;
   f. Measuring the changes in magnitude of a signal from the receive transducer coil, and applying the calibration coefficients to those changes to produce calibrated changes; and
   g. From those calibrated changes, producing a color contour map showing the locations, length, width, and depth of the surface defects in the chosen area.

2. The method according to claim 1, wherein the resonant frequency is 4.2 MHz.

3. The method according to claim 1, wherein the array comprises a square grid with sixteen rows and sixteen columns of transducer coil pairs.

4. The method according to claim 1, further comprising the step of calculating the maximum safe operating pressure of the pipeline.

5. A system for producing a color contour map showing the locations, length, width, and depth of all surface defects within a chosen area of the surface of a high pressure pipeline, comprising:
   a. a flexible printed circuit board;
   b. a two dimensional array of transducers printed on the flexible circuit board, wherein each element of the array comprises a pair of two transducer coils, and wherein each transducer coil pair comprises a send coil aligned on top of a receive coil;
   c. a microprocessor on the flexible printed circuit board, and connected to the array, the microprocessor adapted for storing calibration coefficients for each pair of transducer coils;

d. multiplexers on the flexible printed circuit board, and connected to the array, the multiplexers adapted for addressing each of the coil pairs individually;

e. a microcontroller on the flexible printed circuit board, and connected to the array, the microcontroller adapted for controlling all the functions of the array; and f. a USB interface on the flexible printed circuit board, and adapted for connecting the flexible printed circuit board to a computer, wherein a receive circuit connected to the coils is tuned to a resonant frequency, and the transducer coils operate in a send/receive mode.

6. The system according to claim 5, further comprising means for converting a change in measured resonance to a visual display of the length, depth, and width of the surface defect.

7. The system according to claim 5, further comprising a square grid with sixteen rows and sixteen columns of transducer coil pairs.

8. The system according to claim 5, wherein the resonant frequency is 4.2 MHz.

* * * * *